United States Patent [19]
Hardwicke, III

[11] Patent Number: 5,969,188
[45] Date of Patent: Oct. 19, 1999

[54] PROCESS FOR PRODUCING TRIFLUOROMETHYLACETOPHENONES

[75] Inventor: J. E. Hardwicke, III, Columbia, S.C.

[73] Assignee: NIPA Hardwicke, Inc., Elgin, S.C.

[21] Appl. No.: 09/225,604

[22] Filed: Jan. 5, 1999

[51] Int. Cl.$^6$ .................................................. C07C 45/42
[52] U.S. Cl. ......................... 568/323; 568/335; 568/309; 568/322
[58] Field of Search ..................... 568/323, 335, 568/309, 322; 570/144, 196; 562/864, 849, 855; 564/348; 514/688

[56] References Cited

U.S. PATENT DOCUMENTS

| | | | |
|---|---|---|---|
| 3,616,377 | 10/1971 | Arnold et al. | 204/162 |
| 3,927,133 | 12/1975 | Satomura | 260/669 |
| 4,157,344 | 6/1979 | Feiring | 260/575 |
| 4,207,266 | 6/1980 | Opie | 260/651 |
| 4,454,350 | 6/1984 | Desbois | 568/319 |
| 4,533,777 | 8/1985 | Marhold et al. | 570/144 |
| 4,950,802 | 8/1990 | Nader | 568/655 |
| 5,142,092 | 8/1992 | Kysela et al. | 558/423 |

FOREIGN PATENT DOCUMENTS

| | | | |
|---|---|---|---|
| 02049736 | 2/1990 | Japan | C07B 41/10 |
| 9049736 | 2/1990 | Japan | C07B 41/10 |

OTHER PUBLICATIONS

Collins et al, Tetrahedron Letters, vol. 28 #38 pp. 4391–4394, 1987.
Collins et al, Journal of Organic Chemistry, vol. 55, pp. 3565–3568, 1990.
Aldrich Catalog Handbook of Fine Chemicals, p. 1466, 1996.
"Method for perparation of acetophnone derivatives" Chemical Abstracts 125:114257u, 1996.
"Method for perparation of acetophnone derivatives" Chemical Abstracts 127:294925h, 1997.
Document No. 40221, 1997, Research Disclosure.
Document No. 386014, Jun. 10, 1996, Research Disclosure.

*Primary Examiner*—Shailendra Kumar
*Assistant Examiner*—Sreeni Padmanabhan
*Attorney, Agent, or Firm*—Hedman, Gibson & Costigan, P.C.

[57] ABSTRACT

The present invention provides high purity trifluoromethylacetophenones of the general formula:

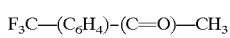

wherein the position of the $CF_3$— group on the aromatic ring may be in the 2-, 3-, or 4- position relative to the acetyl, —(C=O)—$CH_3$, group, said trifluoromethylacetophenone being substantially free of other organic or inorganic materials, wherein said trifluoromethylacetophenones are produced by a novel high yield process.

9 Claims, No Drawings

PROCESS FOR PRODUCING TRIFLUOROMETHYLACETOPHENONES

FIELD OF THE INVENTION

The present invention relates to high purity trifluoromethylacetophenones and a method for their preparation. More specifically, the present invention relates to 3-trifluoromethylacetophenone prepared from 3-trifluoromethylbenzoyl chloride by a two-step high yield process.

BACKGROUND OF THE PRESENT INVENTION

Several processes have been used to produce 3-trifluoromethylacetophenone in the past; however, in all cases the yields have been low (70% or less), the volume efficiency of the processes have been low, and in some cases the product quality has been poor.

Examples include, U.S. Pat. No. 4,207,266, which teaches the reaction of 3-trifluoromethylbenzoyl chloride with the ethoxymagnesium derivative of diethyl malonate to form 3-trifluoromethylbenzoylmalonate. 3-Trifluoromethylbenzoylmalonate is then treated with aqueous acid to produce 3-trifluoromethylacetophenone in 60–70% yield.

Another example is set forth in CA 43:3361e-f, which discloses the addition of methyl Grignard reagent to 3-trifluoromethylphenyl cyanide, followed by acidification with aqueous acetic acid to form 3-trifluoromethylacetophenone in both poor quality and low yield.

A third example is described in Research Disclosure (1997), 402 (Oct) P706 (No. 40221), (CA 127:294925h). This reference teaches the multi-step reaction of 3-trifluoromethylaniline sequentially with a) aqueous sulfuric acid, b) aqueous sodium nitrite, c) aqueous acetaldoxime, d) cuprous sulfate and sodium bicarbonate and e) hydrochloric acid to form 3-trifluoromethylacetophenone in 70% yield. However, the overall volume efficiency of this process scheme is very low.

A fourth reference, Research Disclosure (1996), 386, 348 (CA 125:114257), teaches the reaction of 3-trifluoromethylbromobenzene with magnesium to produce the corresponding Grignard reagent followed by reaction with acetic anhydride and finally with aqueous acetic acid to form 3-trifluoromethylacetophenone. The yield of product from this reaction is about 60%; however, this Grignard reaction is known to be unstable and can decompose explosively. In addition, the reaction with acetic anhydride has to be run very cold, at about 0° C., thus making this route not commercially appealing.

In summary, all of the prior art processes for producing 3-trifluoromethylacetophenone have significant drawbacks. Accordingly, it would represent a notable advance in the state of the art if a simple and efficient process to provide 3-trifluoromethylacetophenone in high yield and high purity starting with readily commercially available reagents were provided.

SUMMARY OF THE PRESENT INVENTION

To this end, the present invention provides high purity trifluoromethylacetophenones which are substantially free of organic and inorganic contaminants. B The present invention also provides a process for producing these high purity trifluoromethylacetophenones, which process comprises the two steps of (a) reacting a trifluoromethylbenzoyl halide with a diorganoamine in the presence of aqueous base to form a N,N-dialkyltrifluoromethylbenzamide and (b) addition of a methyl Grignard reagent to said benzamide followed by acidification with aqueous acetic acid to form the product. Moderate temperatures are used in both steps (a) and (b). The overall yield from the two step process of the present invention is about 90% or higher and the quality of the product is preferably greater than about 98%.

DETAILED DESCRIPTION OF THE PRESENT INVENTION

As used throughout the present specification and claims the phrase "substantially free" means at least about 95% and more preferably at least about 98% pure.

The present invention provides high purity trifluoromethylacetophenones of the general formula:

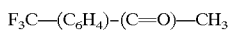
$F_3C—(C_6H_4)—(C=O)—CH_3$ wherein the position of the $CF_3$— group on the aromatic ring may be in the 2-, 3- or 4- position relative to the acetyl, —(C=O)—$CH_3$, group. A preferred trifluoromethylacetophenone of the present invention is 3-trifluoromethylacetophenone.

The present invention also provides a method for producing high purity trifluoromethylacetophenones, the process comprising the steps of (a) reacting a trifluoromethylbenzoyl halide of the general formula:

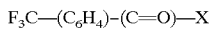
$F_3C—(C_6H_4)—(C=O)—X$ wherein the position of the $CF_3$— group on the aromatic ring may be in the 2-, 3-, or 4- position relative to the acetyl, —(C=O)—$CH_3$, group and X is a halogen atom, selected from the group consisting of fluorine, chlorine, bromine and iodine, with a diorganoamine of the general formula

$R_2NH$ wherein each R is independently a straight or branched chain monovalent aliphatic hydrocarbon group with from 1 to about 6 carbon atoms, in the presence of an aqueous base, used as an acid acceptor, resulting in the formation of N,N-dialkyltrifluoromethylbenzamide of the general formula:

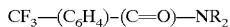
$CF_3—(C_6H_4)—(C=O)—NR_2$ wherein the position of the $CF_3$ group on the aromatic ring may be in the 2-, 3-, or 4- position relative to the acetyl, —(C=O)—$CH_3$, group and each R is independently a straight or branched chain monovalent aliphatic hydrocarbon group with from 1 to about 6 carbon atoms, and (b) addition of a methyl Grignard reagent to said benzamide, followed by acidification with aqueous acetic acid to form the product of the general formula:

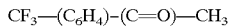
$CF_3—(C_6H_4)—(C=O)—CH_3$ wherein the position of the $CF_3$ group on the aromatic ring may be in the 2-, 3-, or 4- position relative to the acetyl, —(C=O)—$CH_3$, group.

Moderate temperatures, ranging from about ambient to about 60° C., are used in both steps (a) and (b). The trifluoromethylbenzoyl halide reactants are known to those skilled in the art. Particularly useful in the practice of the present invention is 3-trifluoromethylbenzoyl chloride. Exemplary of the bases useful as an acid acceptor, in the practice of the present invention is sodium hydroxide, potassium hydroxide, potassium carbonate, potassium bicarbonate, sodium carbonate, sodium bicarbonate, calcium carbonate, calcium hydroxide, zince oxide, calcium oxide and mixtures thereof in a strength of about 5–70%. The diorganoamine may be any of those within the above-defined formula such as, but not limited to diethylamine, dipropylamine, dimethylamine, dibutylamine, di-tert-butylamine, mixtures of the foregoing and the like. Particularly useful in the practice of the present invention is diethylamine.

Grignard reagents are well known to those skilled in the art and generally comprise organometallic compounds, typically an alkylmagnesium halide. In the practice of the present invention, the Grignard reagents employ methyl as the alkyl constituent.

Acidification is preferably accomplished with acetic acid. However other acidification reagents such as hydrochloric acid, sulfuric acid and ammonium chloride may also be employed in the practice of the present invention.

The overall yield from the two step process is at least about 90% and the quality is greater than about 98%.

The high purity products of the present invention have the advantage of more facile utility as intermediates for the production of several commercially important agricultural herbicides and as intermediates in the pharmaceutical industry wherein purity is of utmost importance.

DESCRIPTION OF THE PREFERRED EMBODIMENTS

The following examples illustrate the present invention. They are not to be construed to limit the scope of the appended claims in any manner whatsoever.

EXAMPLE 1

To a 1 litre flask equipped with a stirrer, two addition funnels, condenser, and heating mantle was added 175 g of water and 75.3 g (1.03 mole) of diethylamine. To this mixture was simultaneously added with stirring 208.5 g (1.0 mole) of 3-trifluoromethylbenzoyl chloride and 81.5 g (1.02) mole of 50% w/w aqueous NaOH. The pH during these additions was maintained between 9–10. The temperature during these additions was maintained between 40° C. and 55° C. On completion of these additions, the mixture was heated at 50–55° C. for 30 minutes with stirring. To the mixture was added 151 g of toluene. After standing for a few minutes two layers formed. The lower aqueous layer was removed. Additional toluene and water was added to the flask with stirring. After standing again for a few minutes the lower aqueous layer was removed. The upper organic layer was then heated under vacuum to remove toluene. After complete removal of the toluene from the upper layer there remained 239 g (0.975 mole) of 99.35% pure N,N-diethyl-3-trifluoromethylbenzamide.

EXAMPLE 2

To a 2 liter flask equipped with a stirrer, condenser, dry nitrogen overgas, and a subsurface addition tube was added 616 g of tetrahydrofuran, 35.5 g of magnesium chips and a few crystals of iodine. The mixture was heated to 50° C. with gentle stirring. To this mixture was added 74 g (1.47 mole) of methyl chloride by subsurface addition, maintaining the temperature between 50° C.–60° C. The resultant methyl magnesium Grignard reagent was cooled to 30° C. To this Grignard solution was added with stirring 239 g (0.975 mole) of N,N-diethyl-3-trifluoromethylbenzamide over a one hour period. After complete addition the mixture was heated and stirred for 18 hours at 35° C. to 40° C.

To another 2 litre flask, similarly equipped, was added 181 g of acetic acid and 413 g of water. With stirring, the above mixture was added to this flask. The resultant mixture was then allowed to separate. The lower aqueous layer was removed, and the upper organic layer was then washed several times with a saturated aqueous sodium chloride solution. The organic layer was then heated under vacuum to remove tetrahydrofuran. After removal of the solvent, the product mixture was distilled under vacuum yielding 169.8 g (0.90 mole) of 98.7% pure 3-trifluoromethylacetophenone.

Many variations of the present invention will suggest themselves to those skilled in the art in light of the above-detailed description. All such obvious modifications are within the full intended scope of the appended claims.

All of the above-referenced patents, patent applications and publications are hereby incorporated by reference.

I claim:

1. A process for the production of a trifluoromethylacetophenone at a purity of at least about 90% and yield of at least about 90% of the general formula:

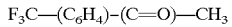

wherein the position of the $CF_3$— group on the aromatic ring may be in the 2-, 3-, or 4- position relative to the acetyl, —(C=O)—$CH_3$, group, said process comprising the steps of:

(a) reacting a trifluoromethylbenzoyl halide of the general formula:

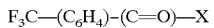

wherein the position of the $CF_3$— group on the aromatic ring may be in the 2-, 3-, or 4- position relative to the acetyl, —(C=O)—$CH_3$, group and X is a halogen atom selected from the group consisting of fluorine, chlorine, bromine, and iodine, with a diorganoamine of the general formula

wherein each R is independently a straight or branched chain monovalent aliphatic hydrocarbon with from 1 to about 6 carbon atoms in the presence of an aqueous base, used as an acid acceptor, resulting in the formation of a N,N-dialkyltrifluoromethylbenzamide of the general formula:

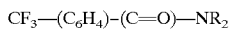

wherein the position of the $CF_3$— group on the aromatic ring may be in the 2-, 3-, or 4- position relative to the acetyl, —(C=O)—$CH_3$, group, and each R is as defined above; and (b) adding a methyl Grignard reagent to said benzamide followed by acidification with an aqueous acidification reagent to form said trifluoromethylacetophenone product.

2. A process as defined in claim 1 wherein said trifluoromethylbenzoyl halide comprises 3-trifluoromethylbenzoyl chloride.

3. A process as defined in claim 1 wherein said diorganoamine comprises diethylamine.

4. A process as defined in claim 1 wherein said N,N-dialkyltrifluoromethylbenzamide comprises N,N-diethyl-3-trifluoromethylbenzamide.

5. A process as defined in claim 1 wherein said trifluoromethylacetophenone comprises 3-trifluoromethylacetophenone.

6. A process as defined in claim 1 wherein said trifluoromethylacetophenone product is at least about 95% free of other organic and inorganic compounds.

7. A process as defined in claim 5 wherein said 3-trifluoromethylacetophenone is produced in a yield of at least about 90%.

8. A process as defined in claim 1 wherein said base is selected from the group consisting of sodium hydroxide, potassium hydroxide, potassium carbonate, potassium bicarbonate, sodium carbonate, sodium bicarbonate, calcium carbonate, calcium hydroxide, zinc oxide, calcium oxide and mixtures of any of the foregoing.

9. A process as defined in claim 1 wherein said acidification reagent is selected from the group consisting of acetic acid, hydrochloric acid, sulfuric acid, ammonium chloride and mixtures of any of the foregoing.

\* \* \* \* \*